United States Patent

Yamamoto et al.

[11] Patent Number: 4,847,366
[45] Date of Patent: Jul. 11, 1989

[54] 5-FLUOROURIDINE DERIVATIVE AND PREPARATION OF THE SAME

[75] Inventors: Yoshihiro Yamamoto; Kazuhiro Shimokawa, both of Settsu; Kunitada Tanaka, Osaka; Yorisato Hisanaga, Ibaraki, all of Japan

[73] Assignee: Daikin Industries Ltd., Osaka, Japan

[21] Appl. No.: 81,730

[22] Filed: Aug. 5, 1987

[30] Foreign Application Priority Data

Aug. 5, 1986 [JP] Japan .................. 61-184904

[51] Int. Cl.⁴ .................. C07H 19/06; A61K 31/70
[52] U.S. Cl. .................................................. 536/23
[58] Field of Search ............................ 536/23; 514/50

[56] References Cited

U.S. PATENT DOCUMENTS 3,221,010  11/1965  Duschinsky ................ 536/23

FOREIGN PATENT DOCUMENTS 0111299  6/1984  European Pat. Off. .
0151189  8/1985  European Pat. Off. .
0147774  4/1981  Fed. Rep. of Germany ........ 536/23
0140098  8/1983  Japan ..................... 536/23
0004198  1/1985  Japan ..................... 514/50
0138481  6/1987  Japan ..................... 536/24

Primary Examiner—Herbert J. Lilling
Attorney, Agent, or Firm—Birch, Stewart, Kolasch & Birch

[57] ABSTRACT

A novel 5-fluorouridine derivative of the formula:

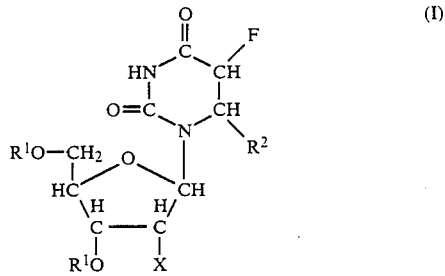

wherein $R^1$ is a $C_1$–$C_{10}$ aliphatic carbonyl group, $R^2$ is a fluorine atom or a $C_1$–$C_3$ aliphatic carbonyloxy group, and x is a halogen atom such as a fluorine, chlorine, bromine and iodine atom, which is useful as an intermediate in the preparation of a 5-fluoro-2'-deoxyuridine derivative which is useful as an anticancer agent.

15 Claims, No Drawings

5-FLUOROURIDINE DERIVATIVE AND PREPARATION OF THE SAME

BACKGROUND OF THE INVENTION

1. Field of the Invention

The present inventions relates to a novel 5-fluorouridine derivative and a process for preparing the same. The novel 5-fluorouridine derivative can be used as an intermediate in the preparation of a 5-fluoro-2′-deoxyuridine derivative which is useful as an anticancer agent.

2. Description of the Prior Art

The 5-fluoro-2′-deoxyuridine derivative may be prepared according to following reaction scheme:

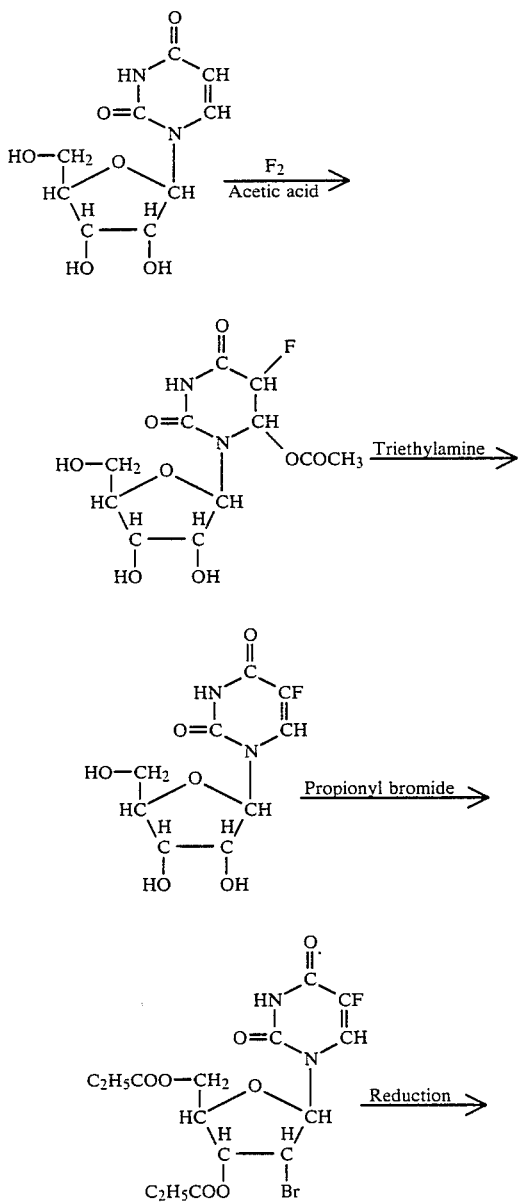

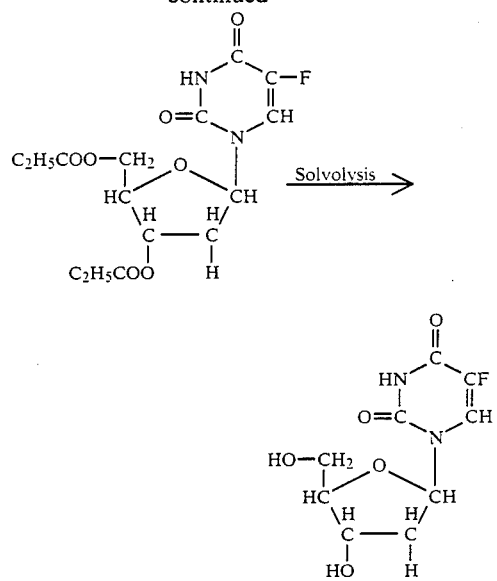

(cf. Bull. Chem. Soc. Japan, 50, 2197 (1977)).

In the above conventional method, since the solubility of uridine in acetic acid is small, productivity per unit volume of reactant is low. Further, it is difficult to separate the compound obtained by the reaction with triethylamine after the fluorination from triethylamine acetate by a simple separation manner such as washing with water. Therefore, the purity of the final product is poor.

SUMMARY OF THE INVENTION

One object of the present invention is to provide a novel 5-fluorouridine derivative, which is conveniently used for the production of a 5-fluoro-2′-deoxyuridine derivative.

Another object of the present invention is to provide a process for producing a novel 5-fluorouridine derivative.

According to one aspect of the present invention, there is provided a novel 5-fluorouridine derivative of the formula:

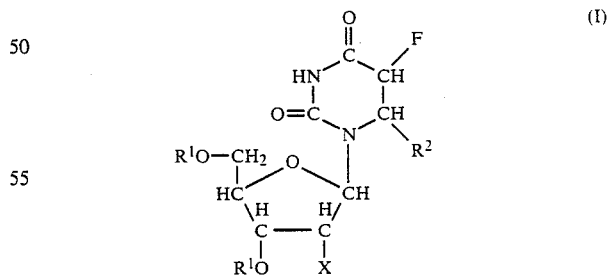

wherein $R^1$ is a $C_1$-$C_{10}$ aliphatic carbonyl group, $R^2$ is a fluorine atom or a $C_1$-$C_3$ aliphatic carbonyloxy group, and X is a halogen atom such as a fluorine, chlorine, bromine and iodine atom.

According to the second aspect of the present invention, there is provided a process for preparing a 5-fluorouridine derivative of the formula (I) comprising reacting a uridine derivative of the formula:

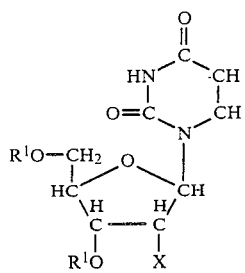

(II)

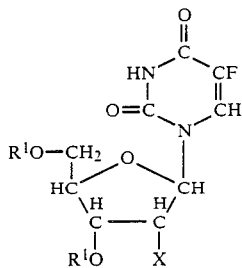

(III)

wherein $R^1$ and X are the same as defined above with a electrophilic fluorinating agent in a $C_1$–$C_3$ aliphatic carboxylic acid as a solvent.

DETAILED DESCRIPTION OF THE INVENTION

The present invention is based on the finding that the compound prepared by reacting uridine and the aliphatic carbonyl halide is very soluble in acetic acid, and that the compound produced by the reaction with triethylamine after fluorination can be easily separated from a by-product, namely the triethylamine salt of acetic acid.

The uridine derivative (II) used as a starting material in the process of the present invention may be prepared by reacting uridine with a $C_1$–$C_{10}$ carboxyl halide in acetonitrile (cf. Japanese Patent Publication No. 39707/1980).

In the present specification, the "electrophilic fluorinating agent" is used to have the same meaning as that used conventionally in this field and includes, for example, $F_2$, $FClO_3$, $CF_3COF$, $CF_3COOF$ and $CH_3COOF$. Among them, $F_2$ is preferable since it is easily available. In use, $F_2$ is preferably diluted with an inert gas (e.g. nitrogen, helium, argon, etc.) to a concentration of 1 to 20% by volume.

According to the reaction of the present invention, the $C_1$–$C_3$ aliphatic carbonyloxy group emanated from the solvent is added at the 6-position. When $F_2$ is used as the electrophilic fluorinating agent, a compound in which a fluorine atom is added to the 6-position is by-produced. A molar ratio of the uridine derivative (II) to the electrophilic fluorinating agent is 1:1 to 1:5.

The reaction of the present invention is carried out usually at a temperature of 0° to 40° C. Therefore, acetic acid is a preferable solvent since it has a comparatively low melting point.

The novel 5-fluorouridine derivative (I) of the present invention may be recovered by removing the solvent by, for example, distillation under reduced pressure, and then reacted with an organic base (e.g. triethylamine, morpholine, etc.) in a solvent (e.g. chloroform, methanol, ethyl acetate, etc.) at a temperature of 0° to 40° C. to prepare a compound of the formula:

wherein $R^1$ and X are the same as defined above. In this reaction, a salt such as triethylamine salt of acetic acid is by-produced but can be easily removed from the compound (III) by washing the reaction mixture with water since the compound (III) is insoluble in water.

Subsequently, the compound (III) is reduced and then hydrolyzed by conventional methods to obtain the 5-fluoro-2'-deoxyuridine derivative (cf. Japanese Patent Publication No. 39707/1980). When X is bromine or iodine, the reduction of the compound (III) easily proceeds.

The present invention will be explained further in detail by following examples.

EXAMPLE 1

In a solution of a compound (1.5 g, 3.5 mol) of the formula:

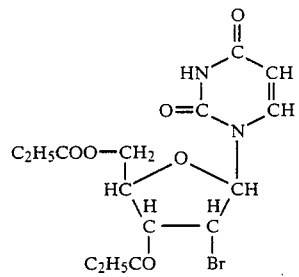

is glacial acetic acid (20 g) kept at a temperature of 12° to 15° C., nitrogen containing 10% by volume of fluorine was bubbled at a flow rate of 40 ml/min. for 30 minutes (fluorine=5.36 mol).

To the reaction mixture, calcium carbonate (200 mg) was added and suspended, and acetic acid was removed at 40° C. under reduced pressure of 40 mmHg (or atm.).

To the residue, ethyl acetate (40 ml) was added, and undissolved materials were filtered off. From the filtrate, ethyl acetate was evaporated off at 40° C. under reduced pressure of 40 mmHg to obtain a crystalline material (1.8 g).

$^1$H-NMR and $^{19}$F-NMR analyses of the crystalline material revealed that it was a mixture of the 5-fluorouridine derivatives of the formulas (molar ratio of about 1:1):

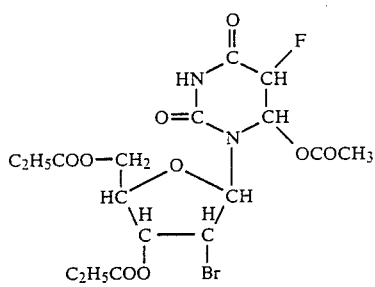 (1)

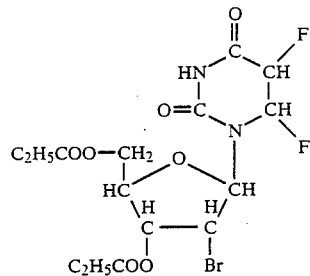 (2)

NMR data for 5-fluorouridine derivative (1):

$^1$H-NMR (CDCl$_3$): δ(ppm)=1.16 (t, 3H, —COCH$_2$CH$_3$), 1.18 (t, 3H, —COCH$_2$CH$_3$), 2.15 (s, 3H, —COCH$_3$), 4.32–4.45 (m, 3H, H$_{4'}$, H$_{5'}$), 4.60 (d, 1H, H$_{2'}$), and 6.25 (d, 1H, H$_{1'}$).

$^{19}$F-NMR (Standard: trifluoroacetic acid, solvent: CDCl$_3$): δ(ppm)=131.4 and 113.3.

NMR data for 5-fluorouridine derivative (2):

$^1$H-NMR (CDCl$_3$): δ(ppm)=1.16 (t, 3H, —COCH$_2$CH$_3$), 1.18 (t, 3H, —COCH$_2$CH$_3$), 2.15 (s, 3H, —COCH$_3$), 4.34–4.52 (m, 3H, H$_{4'}$, H$_{5'}$), 4.62 (t, 1H, H$_{2'}$), and 6.22 (d, 1H, H$_{1'}$).

$^{19}$F-NMR (Standard: trifluoroacetic acid, solvent: CDCl$_3$): δ(ppm)=132.3, 76.2 and 75.8.

EXAMPLE 2

The crystalline material produced in Example 1 (1.8 g) was added to a mixture of triethylamine and methanol in a volume ratio of 1:1 and stirred at 20°–25° C. for 2 hours. From the reaction mixture, an organic material was extracted with chloroform and washed with water followed by removal of chloroform to obtain a crystalline compound, which was recrystallized from ethanol to obtain a compound (1.1 g) of the formula:

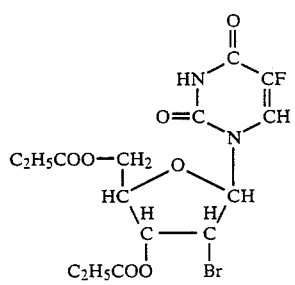

EXAMPLE 3

In a solution of a compound (1.6 g, 3.5 mol) of the formula:

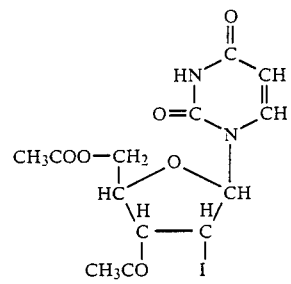

is glacial acetic acid (20 g) kept at a temperature of 12° to 15° C., nitrogen containing 10% by volume of fluorine was bubbled at a flow rate of 40 ml/min. for 30 minutes (fluorine=5.36 mol).

To the reaction mixture, calcium carbonate (200 mg) was added and suspended, and acetic acid was removed at 40° C. under reduced pressure of 40 mmHg (or atm.).

To the residue, ethyl acetate (40 ml) was added, and undissolved materials were filtered off. From the filtrate, ethyl acetate was evaporated off at 40° C. under reduced pressure of 40 mmHg to obtain a crystalline material (1.3 g).

$^1$H-NMR and $^{19}$F-NMR analyses of the crystalline material revealed that it was a mixture of the 5-fluorouridine derivatives of the formulas (molar ratio of about 1:1):

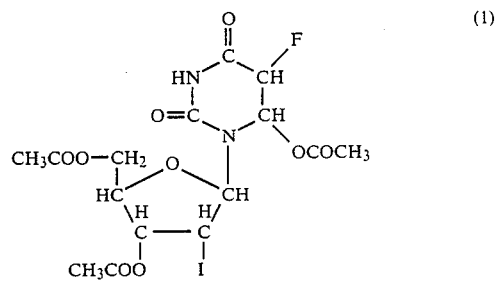 (1)

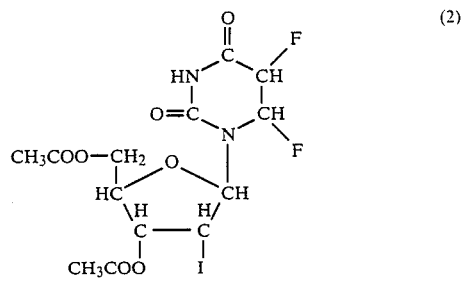 (2)

NMR data for 5-fluorouridine derivative (1):

$^1$H-NMR (CDCl$_3$): δ(ppm)=2.0 (s, 3H, —COCH$_3$), 2.05 (s, 3H, —COCH$_3$), 2.15 (s, 3H, —COCH$_3$), 4.32–4.45 (m, 3H, H$_{4'}$, H$_{5'}$), 4.55 (d, 1H, H$_{2'}$), and 6.25 (d, 1H, H$_{1'}$).

$^{19}$F-NMR (Standard: trifluoroacetic acid, solvent: CDCl$_3$): δ(ppm)=131.4 and 113.3.

NMR data for 5-fluorouridine derivative (2):

$^1$H-NMR (CDCl$_3$): δ(ppm)=2.0 (s, 3H, —COCH$_3$), 2.05 (s, 3H, —COCH$_3$), 2.15 (s, 3H, —COCH$_3$), 4.34–4.52 (m, 3H, H$_{4'}$, H$_{5'}$), 4.58 (t, 1H, H$_{2'}$), and 6.22 (d, 1H, H$_{1'}$).

$^{19}$F-NMR (Standard: trifluoroacetic acid, solvent: CDCl$_3$): δ(ppm)=132.3, 76.2 and 75.8.

EXAMPLE 4

The crystalline material produced in Example 3 (1.3 g) was added to a mixture of triethylamine and methanol in a volume ratio of 1:1 and stirred at 20°–25° C. for 2 hours. From the reaction mixture, an organic material was extracted with chloroform and washed with water followed by removal of chloroform to obtain a crystalline compound, which was recrystallized from ethanol to obtain a compound (0.8 g) of the formula:

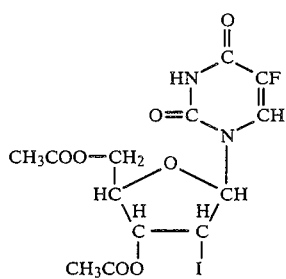

What is claimed is:

1. A 5-fluorouridine derivative of the formula:

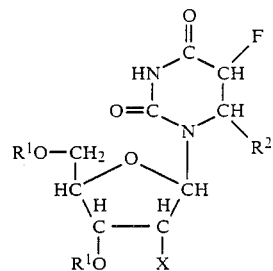

wherein $R^1$ is a $C_1$–$C_{10}$ aliphatic carbonyl group, $R_2$ is a fluorine atom or a $C_1$–$C_3$ aliphatic carbonyloxy group, and X is a bromine atom or an iodine atom.

2. The derivative according to claim 1, wherein $R^1$ is a methylcarbonyl or an ethylcarbonyl group.

3. The derivative according to claim 1, wherein $R^2$ is a fluorine atom or a methylcarbonyloxy group.

4. The derivative according to claim 2, wherein $R^2$ is a fluorine atom or a methylcarbonyloxy group.

5. The derivative according to claim 1, wherein X is a bromine atom.

6. The derivative according to claim 1, wherein X is an iodine atom.

7. The derivative according to claim 1, wherein $R^1$ is a methylcarbonyl group.

8. The derivative according to claim 1, wherein $R^1$ is an ethylcarbonyl group.

9. The derivative according to claim 5, wherein $R^1$ is an ethylcarbonyl group.

10. The derivative according to claim 6, wherein $R^1$ is a methylcarbonyl group.

11. The derivative according to claim 1, wherein $R^2$ is a fluorine atom.

12. The derivative according to claim 5, wherein $R^2$ is a fluorine atom.

13. The derivative according to claim 6, wherein $R^2$ is a fluorine atom.

14. The derivative according to claim 5, wherein $R^2$ is a methylcarbonyloxy group.

15. The derivative according to claim 6, wherein $R^2$ is a methylcarbonyloxy group.

* * * * *